US00PP25709P2

(12) United States Plant Patent
O'Neill

(10) Patent No.: US PP25,709 P2
(45) Date of Patent: Jul. 14, 2015

(54) ***BOUGAINVILLEA* PLANT NAMED 'VISTA1'**

(50) Latin Name: *Bougainvillea communis*
Varietal Denomination: Vista1

(71) Applicant: Jerome O'Neill, Juana Diaz, PR (US)

(72) Inventor: Jerome O'Neill, Juana Diaz, PR (US)

(73) Assignee: Vista Farms S.E. PR (US)

( * ) Notice: Subject to any disclaimer, the term of this patent is extended or adjusted under 35 U.S.C. 154(b) by 157 days.

(21) Appl. No.: 13/986,855

(22) Filed: Jun. 11, 2013

(51) Int. Cl.
*A01H 5/02* (2006.01)

(52) U.S. Cl.
USPC ..... Plt./256

(58) Field of Classification Search
USPC ..... Plt./256
See application file for complete search history.

*Primary Examiner* — Susan McCormick Ewoldt
(74) *Attorney, Agent, or Firm* — Cassandra Bright

(57) ABSTRACT

A new and distinct *Bougainvillea* cultivar named 'Vista1' is disclosed, characterized by burgundy bracts. Plants are very compact. The new variety is a *Bougainvillea*, typically produced as an ornamental plant.

2 Drawing Sheets

Latin name of the genus and species: *Bougainvillea communis.*

Variety denomination: 'Vista1'.

BACKGROUND OF THE INVENTION

The new cultivar is the product of chance discovery. The new variety originated as naturally occurring whole plant mutation of the unpatented variety *Bougainvillea communis* 'Flame'. The inventor discovered the variety in a commercial planting of the parent variety in Juana Diaz, Puerto Rico in December of 2010.

After identifying the interesting flower color mutation, the inventor observed the single plant mutation for several months. First propagation was performed by vegetative cuttings during June 2011, in Juana Diaz, Puerto Rico. Access to all plants was restricted, as plants were kept in a facility belonging to the inventor and not open to the public.

Through subsequent propagation by vegetative cuttings, multiple generations have been reproduced, which have shown that the unique features of this cultivar are stable and reproduced true to type.

The cultivar 'Vista1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Vista1'. These characteristics in combination distinguish 'Vista1' as a new and distinct *Bougainvillea cultivar:*

1. Very compact growth habit

2. Color of mature bract is burgundy

PARENT COMPARISON

Plants of the new cultivar 'Vista1' are similar to the parent, in most horticultural characteristics. The new variety, however, produces bracts that are burgundy in color, whereas bracts of the parent variety are an orange-red.

COMMERCIAL COMPARISON

Plants of 'Vista1' are similar in some horticultural characteristics to the variety *Bougainvillea* 'Rijnbo710', U.S. Plant Pat. No. 21,009. The new variety, however, produces smaller foliage, and flowers bracts with less purple coloration than 'Rijnbo710'. Additionally, inflorescence of 'Vista1' are not as tightly compact as inflorescence of 'Rijnbo710'. Plants of the new variety are more compact than plants 'Rijnbo710'.

Plants of 'Vista1' are similar in some horticultural characteristics to the variety *Bougainvillea* 'Vista2', U.S. Ser. No. 13/998,814. The new variety, however, produces immature foliage colored near Yellow-Green 144A, whereas 'Vista2' produces immature foliage colored near Greyed-Orange 175A. Additionally, floral bracts of 'Vista1' are primarily colored near Red 46A, whereas floral bracts of 'Vista2' are colored near Orange N25A and Orange 28A.

BRIEF DESCRIPTION OF THE PHOTOGRAPHS

Figure 1:
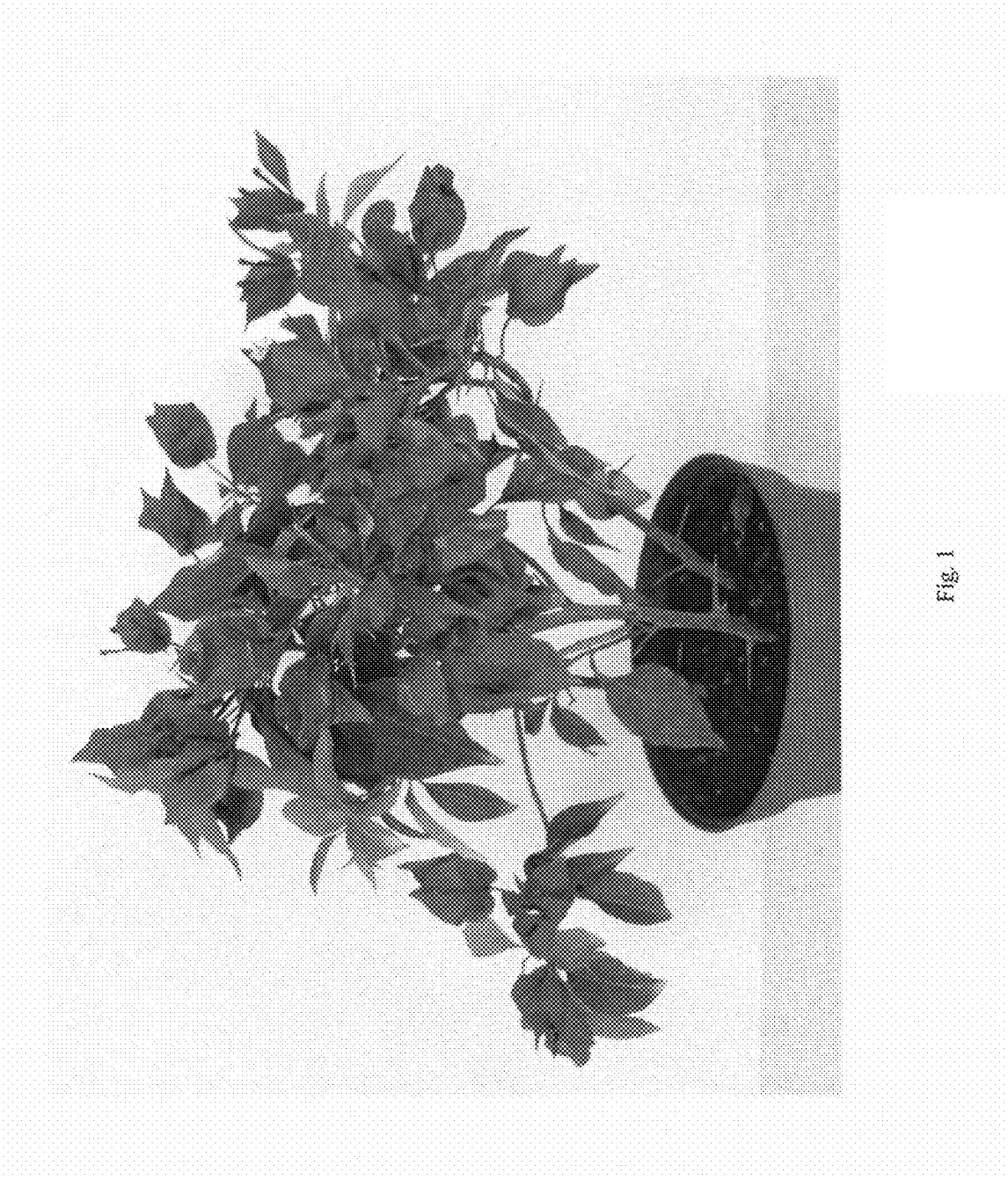

The accompanying photograph in FIG. 1 illustrates in full color a typical plant of 'Vista1' grown in a commercial greenhouse in Juana Diaz, Puerto Rico. This plant is approximately 6 months old, shown planted in a 6 inch container.

Figure 2:
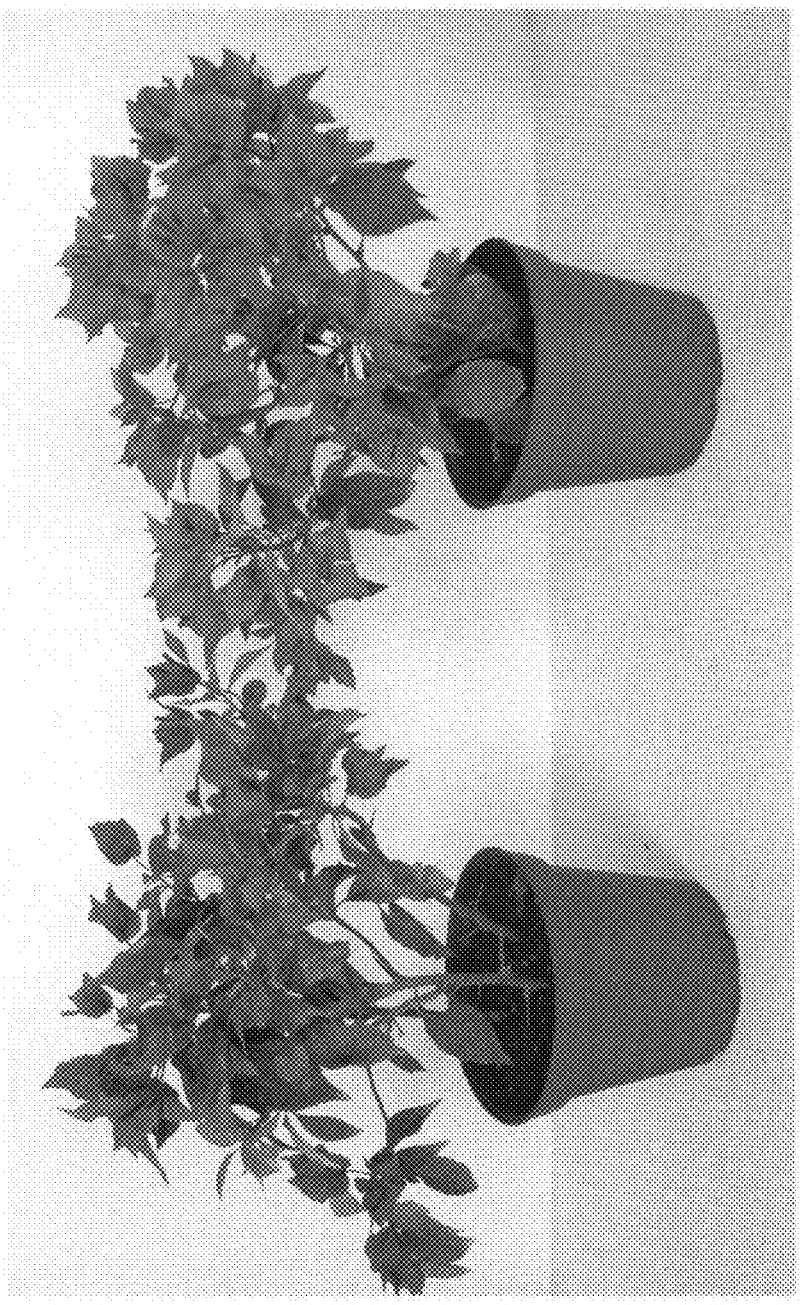

FIG. 2 illustrates plants of 'Vista1' and the parent variety, 'Flame'. 'Vista1' is the plants pictured on the left side of the photograph. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a 'Vista1' plant. This plant was grown in a greenhouse in a commercial 6 inch pot, in Juana Diaz, Puerto Rico. The plant described is approximately 6 months old. Temperatures ranged from 15° C. at night and 18° C. to 24° C. during the day. No artificial light, photoperiodic treatments were given to the plants. Measurements and numerical values represent averages of typical plant types.

Botanical classification: *Bougainvillea communis* 'Vista1'.

PROPAGATION

Time to initiate roots: 14-21 days at approximately 25° C.

Root description: Roots are fine, fibrous and well branched.

PLANT

Growth habit: This plant is an upright tender perennial, suitable for indoor ornamental use, or outdoor garden use in warm climates.

Pot size of plant described: 6 inch.

Height: 22 cm.

Plant spread: 32 cm.

Main stem color: Greyed-Green 198A.

Main stem texture: Smooth, scaly.

Branching characteristics: Not free branching, moderate branching can be achieved with pinching.

Length of primary lateral branches: 8-12 cm.

Quantity of primary lateral branches: 3 per plant.

Characteristics of primary lateral branches:

*Diameter*.—Approximately. 0.3 cm.

*Color*.—Brown N200C.

*Texture*.—Dull, scaly.

Internode length: 1.0-2 cm.

FOLIAGE

Leaf:

*Arrangement*.—Alternate, simple.

*Quantity*.—Approximately 16 per branch.

*Average length*.—Approximately 1.7 cm.

*Average width*.—Approximately. 2.5 cm.

*Shape of blade*.—Elliptical.

*Apex*.—Acute.

*Base*.—Acute.

*Margin*.—Entire.

*Texture of top surface*.—Smooth.

*Texture of bottom surface*.—Smooth.

*Appearance of top surface*.—Glossy.

*Appearance of bottom surface*.—Matte.

*Color*.—Young foliage upper side: Yellow-green near RHS 144A. Young foliage under side: Yellow-green near RHS 144B. Mature foliage upper side: Between RHS Green 137A and RHS green 147A. Mature foliage under side: Near 147B RHS.

*Venation*.—Type: Pinnate. Venation color upper side: RHS Yellow-Green 144B. Venation color under side: RHS Yellow-Green N144B.

*Petiole*.—Length: 1.5 cm. Diameter: 0.2 cm. Color: near RHS Yellow-Green 145A. Texture: Smooth, scaly.

Other characteristics:

Thorns: One thorn is above each leaf. Thorn is pointed downwards; Young thorns are soft. Old thorns are very sharp and strong.

*Average thorn length*.—1.5-2.0 cm.

*Average thorn width at base*.—0.2 cm.

*Thorn coloration*.—Young thorns near RHS Grey-Brown N199C. Old thorns RHS Grey-Brown N199A.

FLOWER

Normal flowering period: Continuously from early Spring through Fall.

Inflorescence:

*Form*.—Axillary, compact cyme.

*Width of entire inflorescence*.—10 cm.

*Height of entire inflorescence*.—11 cm.

*Quantity of individual flowers in inflorescence*.—Avg. 3 on a 6 month old plant.

Flower longevity on plant: Approximately 10 days.

Quantity of inflorescence per plant: Avg. 4.

Persistent or self-cleaning: Self-cleaning.

Bud:

*Shape*.—Oblanceolate with sharp apex.

*Length*.—0.4 cm.

*Diameter*.—0.3 cm.

*Color*.—RHS Red-Purple 60A.

Individual true flower:

*Form/type*.—Single, tubular flowers growing from the base of a single bract. The flowers have no petals or sepals. The individual true "flower" is small, and each cluster of three flowers is surrounded by three bracts. Sometimes the cluster consists of more flowers but the number of bracts is nearly always 3.

*Diameter*.—0.9 cm.

*Depth*.—0.25 cm.

*Days lasting on plant*.—Approximately one week.

Petals: No petals.

Bracts:

*Days lasting on plant*.—Approximately 10, self-cleaning.

*Shape*.—Deltoid.

*Length*.—3.5 cm.

*Width*.—2 cm.

*Tip*.—Acute.

*Base*.—Acute.

*Margin*.—Entire.

*Aspect*.—Undulated.

*Color*.—RHS Red 46A.

*Under side of immature bract*.—RHS Red-Purple 60A.

*Upper side of immature bract*.—RHS Red-Purple 60B.

*Under side of mature bract*.—RHS Red 46A.

*Upper side of mature bract*.—RHS Red 46A.

*Bract vein color on under side*.—RHS Red 53A.

*Bract vein color on upper side*.—RHS Red 53A.

Sepals: No sepals observed.

Peduncles:

*Length*.—5 cm.

*Diameter*.—0.2 cm.

*Angle*.—Approximately 70-90° to the lateral branch.

*Strength*.—Moderately strong.

*Texture*.—Smooth.

*Color*.—Near RHS Green 143C.

Pedicels:

*Arrangement*.—Individual flowers in whorls of 3, together on pedicels. Each individual flower sessile, implanted in a colorful bract.

*Length*.—2.5 cm.

*Diameter*.—0.1 cm.

*Angle*.—Average angle of 45 degrees.

*Strength*.—Moderately strong.

*Color*.—Near RHS Red 46A.

Fragrance: None.

REPRODUCTIVE ORGANS

Stamens:

*Number*.—Average 8.

Anthers:

*Length*.—Approximately 0.05 cm.

*Color*.—Near Yellow-Green 150B.

*Pollen*.—Color RHS Yellow 12A. Quantity: Scant.

Pistil:

*Number*.—1.

*Length*.—0.5 cm.

*Style*.—Length: 0.1 cm. Color: RHS Yellow-Green 145C.

*Stigma*.—Shape: Lineate. Color: Near RHS Yellow Green 146C. Ovary Color: Near RHS Yellow Green 145B.

OTHER CHARACTERISTICS

Seeds and fruits: Seed production not observed.

Disease/pest resistance: Neither resistance nor susceptibility to diseases or pests has been observed in this variety.

Temperature tolerance: Tolerates high temperatures to at least 35 degrees Celsius. Frost is not tolerated. When roots are frozen completely, the plant will not recover.

Drought tolerance: No drought tolerance. Leaves and bracts will drop off the plant immediately under dry conditions.

What is claimed is:

1. A new and distinct cultivar of *Bougainvillea* plant named 'Vista1' as herein illustrated and described.

* * * * *